United States Patent
McCormick

(10) Patent No.: US 7,927,564 B2
(45) Date of Patent: Apr. 19, 2011

(54) HISTOLOGICAL SPECIMEN CASSETTE

(75) Inventor: James B. McCormick, Lincolnwood, IL (US)

(73) Assignee: Leica Biosystems Richmond, Inc., Richmond, IL (US)

( * ) Notice: Subject to any disclaimer, the term of this patent is extended or adjusted under 35 U.S.C. 154(b) by 1031 days.

(21) Appl. No.: 11/311,055

(22) Filed: Dec. 19, 2005

(65) Prior Publication Data

US 2007/0140920 A1   Jun. 21, 2007

(51) Int. Cl.
- *B01L 9/00* (2006.01)
- *B01L 99/00* (2006.01)
- *B01D 12/00* (2006.01)
- *C12Q 1/68* (2006.01)
- *G01N 1/30* (2006.01)

(52) U.S. Cl. ........ 422/561; 422/569; 422/275; 422/302; 422/50; 435/40.52

(58) Field of Classification Search .................. 422/102; 435/40.52

See application file for complete search history.

(56) References Cited

U.S. PATENT DOCUMENTS

| | | | |
|---|---|---|---|
| 4,220,252 A | 9/1980 | Beall | |
| 4,421,246 A | 12/1983 | Schultz | |
| 4,801,553 A * | 1/1989 | Owen et al. | 436/174 |
| 5,080,869 A * | 1/1992 | McCormick | |
| 5,127,537 A | 7/1992 | Graham | |
| 5,269,671 A * | 12/1993 | McCormick | |
| 5,427,742 A | 6/1995 | Holland | |
| 5,665,398 A * | 9/1997 | McCormick | |
| 5,928,934 A * | 7/1999 | McCormick | |
| D448,487 S | 9/2001 | Saez et al. | |
| 6,395,234 B1 * | 5/2002 | Hunnell et al. | 422/101 |
| 6,875,583 B2 * | 4/2005 | Giberson et al. | 435/40.5 |
| 2002/0162843 A1 | 11/2002 | Alley | |
| 2005/0112031 A1 * | 5/2005 | McCormick | |
| 2005/0112034 A1 * | 5/2005 | McCormick | |
| 2007/0116612 A1 * | 5/2007 | Williamson | 422/102 |
| 2008/0254504 A1 * | 10/2008 | Vom et al. | 435/40.52 |

FOREIGN PATENT DOCUMENTS

EP   0312109   4/1989
WO   WO 2004028693 A1 *   4/2004

* cited by examiner

*Primary Examiner* — Jill Warden
*Assistant Examiner* — Dean Kwak
(74) *Attorney, Agent, or Firm* — Thompson Coburn LLP

(57) ABSTRACT

A histological specimen cassette for use in connection with a larger histological specimen cassette, wherein each histological specimen cassette has an internal chamber that includes a receptacle and a lid, the receptacle having a bottom wall, opposite side walls, opposite front and back walls, and an internal chamber or cavity, where the internal chamber or cavity is positioned between the sidewalls, the front and back walls and partially bound by the bottom wall, having a plurality of apertures that extend through the bottom wall and that create fluid passageways into the cavity, the lid having a plurality of apertures that extend through the lid and that create additional fluid passageways into the cavity, the histological specimen cassette being dimensioned such that the histological specimen cassette can fit entirely within the void of the larger histological specimen cassette when the lid is in the closed position.

6 Claims, 4 Drawing Sheets

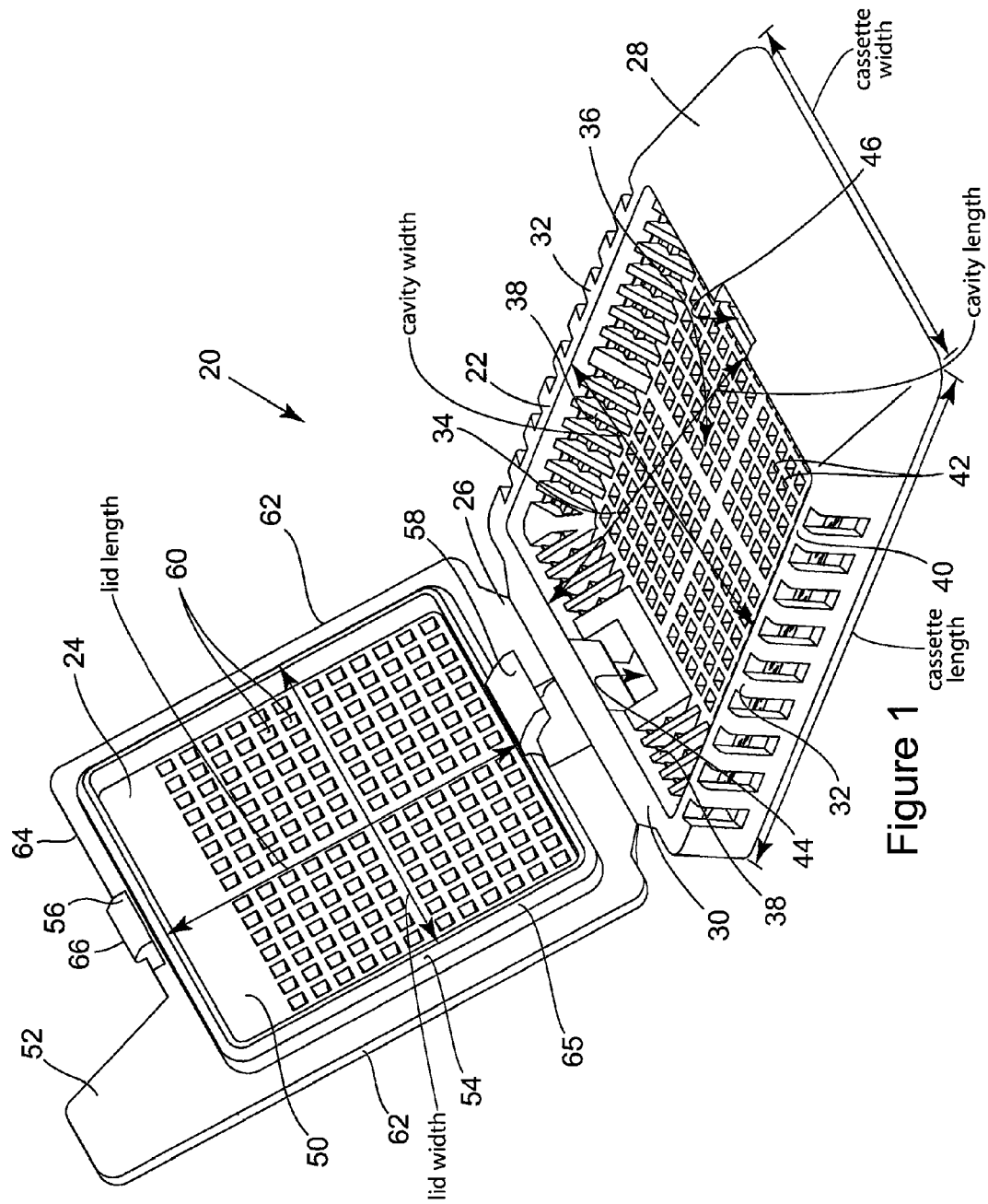

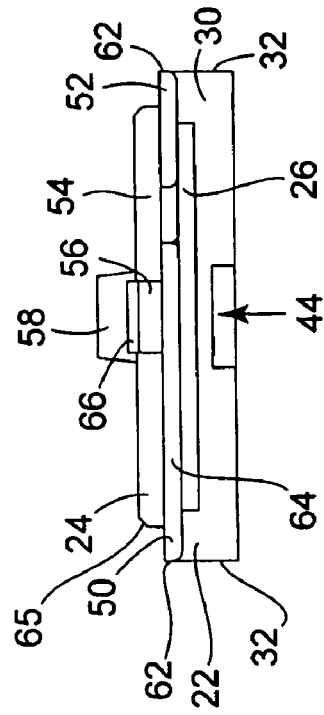
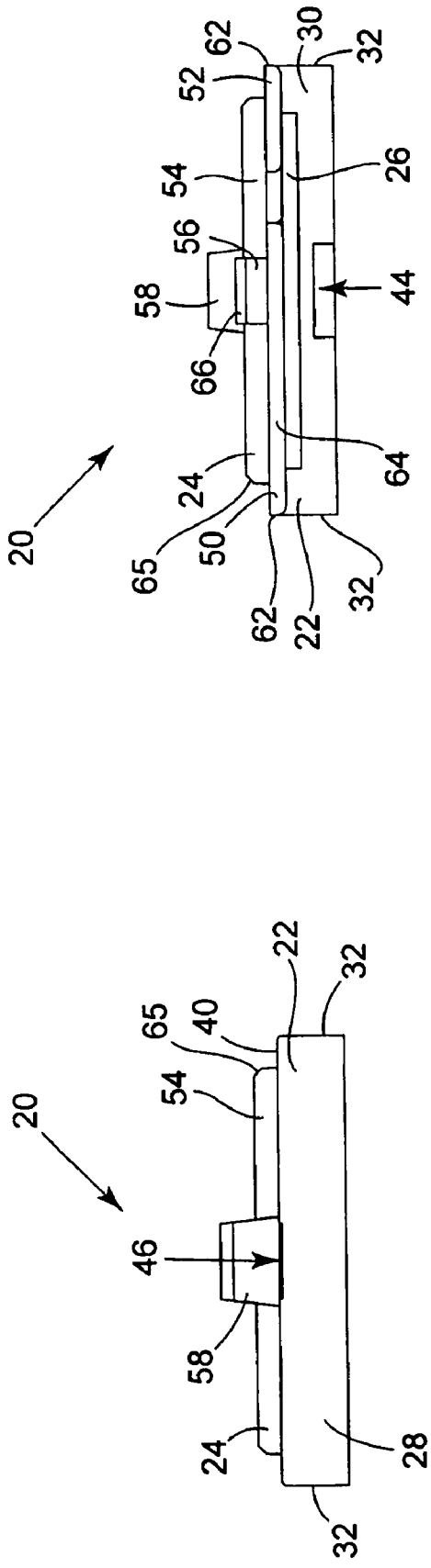
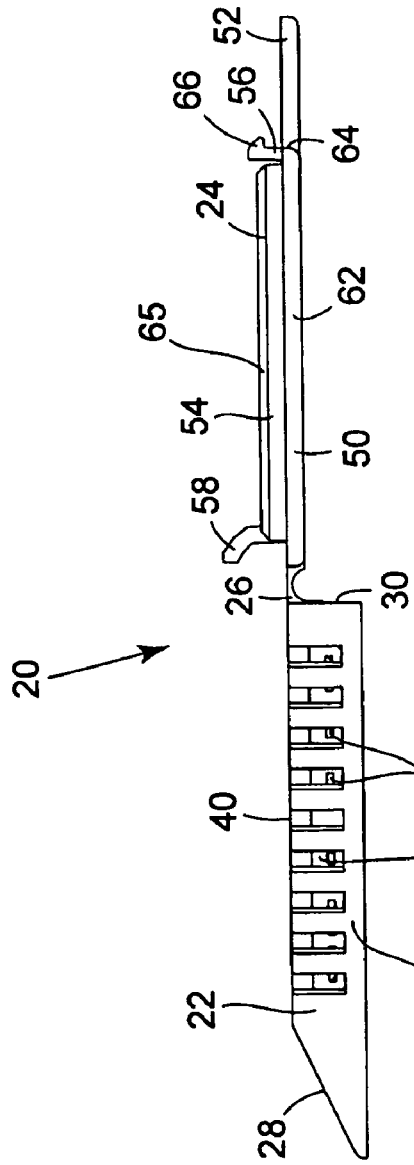

HISTOLOGICAL SPECIMEN CASSETTE

TECHNICAL FIELD OF THE INVENTION

The present invention pertains to the field of histological examination. More particularly, this invention pertains to cassettes for treating tissue samples in preparation of microscopic histological examination.

BACKGROUND OF THE INVENTION

Cassettes of the type disclosed in U.S. Pat. No. 5,928,934 and 5,665,398, the disclosures of which are incorporated herein by reference in their entireties, are used to store, treat, and hold tissue samples in preparation of performing microscopic histological examination of such tissue. Typically, a cassette comprises a receptacle portion that forms a cavity and a lid. The receptacle and lid each typically have numerous small apertures that allow fluid to pass through the cassette and into the cavity. The lid is often attached to the receptacle by a hinge in a manner such that the lid can be used to selectively open and close the cavity of the receptacle.

During the treatment of a tissue sample in preparation of microscopic examination, the tissue sample is typically placed in the cavity of a cassette with the lid of the cassette closed to prevent the tissue sample from inadvertently falling out of the cavity. The cassette is then typically immersed in sequence any number of various fluids such as formaldehyde, ethanol, xylene, and molten paraffin. The apertures in the receptacle and lid of the cassette allow such fluids to pass into the cavity of the cassette and make contact with the tissue sample. In the timing of these steps, a tissue sample is dehydrated, cleared and infiltrated with molten wax within the cassette. Multiple tissue samples in multiple cassettes can be treated in this manner simultaneously.

The treatment procedures typically concludes with the tissue sample resting in molten paraffin. The lid of the cassette is thereafter opened and the tissue sample is removed from the cassette and placed in the cavity of an embedding mold. The cassette is then placed above the tissue sample in the embedding mold and additional paraffin is used to secure the tissue sample to the bottom surface of the cassette. This additional paraffin is allowed to solidify in and around the apertures of the receptacle and thereby provides a firm attachment of the tissue sample to the cassette. As such, the cassette can then be used to hold the wax infiltrated tissue sample as an investment casting of the tissue sample to be sliced by a microtome.

SUMMARY OF INVENTION

The present invention is directed to an improved histological examination cassette. In one aspect of the invention, a histological specimen cassette is configured and adapted for use in connection with a larger specimen cassette that has an internal chamber that creates a parallelepiped void that typically has a length of at least 31.75 millimeters, a width of at least 25.4 millimeters, and a height of at least 5.08 millimeters. The histological specimen cassette comprises a receptacle and a lid. The receptacle has a bottom wall, opposite side walls, opposite front and back walls, and a cavity. The cavity is positioned between the sidewalls and between the front and back walls of the receptacle and is partially bound by the bottom wall. The bottom and top walls have a plurality of apertures that extend through the bottom and top walls and that create fluid passageways into the cavity. The lid also has a plurality of apertures that extend through the lid and that create additional fluid passageways into the cavity. The lid is movable between an opened position and a closed position relative to the receptacle. When the lid is in the closed position, the lid engages the receptacle and the cavity is partially contained by the lid. The histological specimen cassette is dimensioned such that the histological specimen cassette can fit entirely within the void of the larger specimen cassette when the lid is in the closed position.

In another aspect of the invention, a histological specimen cassette for use in connection with a larger histological specimen cassette is disclosed. The histological specimen cassette includes a receptacle and a lid, the receptacle having a bottom wall, opposite side walls, opposite front and back walls, and a cavity, the cavity being positioned between the sidewalls and between the front and back walls, the cavity being partially bound by the bottom wall, the bottom wall having a plurality of apertures that extend through the bottom wall and that create fluid passageways into the cavity, the lid having a plurality of apertures that extend through the lid and that create additional fluid passageways into the cavity, the lid being movable between an opened position and a closed position relative to the receptacle, the lid engaging the receptacle when the lid is in the closed position and the cavity being partially bound by the lid when the lid is in the closed position, and a larger histological specimen cassette has an internal chamber that includes a receptacle and a lid, the receptacle having a bottom wall, opposite side walls, opposite front and back walls, and an internal chamber, the internal chamber being positioned between the sidewalls, the front and back walls and partially bound by the bottom wall, wherein the internal chamber includes a parallelepiped void that has a length of at least 31.75 millimeters, a width of at least 25.4 millimeters, and a height of at least 5.08 millimeters, the histological specimen cassette being dimensioned such that the histological specimen cassette can fit entirely within the void of the larger histological specimen cassette when the lid is in the closed position.

In yet another aspect of the invention, an assembly is disclosed. The assembly includes a first histological specimen cassette having a receptacle and a lid, the receptacle having a bottom wall, opposite side walls, opposite front and back walls, and a cavity, the cavity being positioned between the sidewalls and between the front and back walls, the cavity being partially bound by the bottom wall, the bottom wall having a plurality of apertures that extend through the bottom wall and that create fluid passageways into the cavity, the lid having a plurality of apertures that extend through the lid and that create additional fluid passageways into the cavity, the lid being movable between an opened position and a closed position relative to the receptacle, the lid engaging the receptacle when the lid is in the closed position and the cavity being partially bound by the lid when the lid is in the closed position, and a second histological specimen cassette having a receptacle and a lid, the receptacle having a bottom wall, opposite side walls, opposite front and back walls, and a cavity, the cavity being positioned between the sidewalls and between the front and back walls, the cavity being partially bound by the bottom wall, the bottom wall having a plurality of apertures that extend through the bottom wall and that create fluid passageways into the cavity, the lid having a plurality of apertures that extend through the lid and that create additional fluid passageways into the cavity, the lid being movable between an opened position and a closed position relative to the receptacle, the lid engaging the receptacle when the lid is in the closed position and the cavity being partially bound by the lid when the lid is in the closed position, wherein the cavity of the second histological specimen cassette has a parallelepiped void that has a length of at least 31.75 millimeters, a width of at least 25.4 millimeters, and a height of at least 5.08 millimeters, wherein the first histological specimen cassette fits entirely within the void of the second histological specimen cassette when the lid is in the closed position to create an assembly.

In yet another aspect of the present invention, an assembly is disclosed. The assembly includes a first histological specimen cassette having a receptacle and a lid, the receptacle having a bottom wall, opposite side walls, opposite front and back walls, and a cavity, the cavity being positioned between the sidewalls and between the front and back walls, the cavity being partially bound by the bottom wall, the bottom and top walls have a plurality of apertures that extend through the bottom and top walls and that create fluid passageways into the cavity, the lid having a plurality of apertures that extend through the lid and that create additional fluid passageways into the cavity, the lid being movable between an opened position and a closed position relative to the receptacle, the lid engaging the receptacle when the lid is in the closed position and the cavity being partially bound by the lid when the lid is in the closed position and a second histological specimen cassette that has an internal chamber that creates a parallelepiped void that has a length of at least 31.75 millimeters, a width of at least 25.4 millimeters, and a height of at least 5.08 millimeters wherein the first histological specimen cassette fits entirely within the void of the second histological specimen cassette when the lid is in the closed position to create the assembly.

Still yet another aspect of the present invention is that a method for utilizing two histological specimen cassettes is disclosed. The method includes placing a first histological specimen cassette entirely within a void of the second histological specimen cassette for histological specimen examination, wherein the first histological specimen cassette comprises a receptacle and a lid, the receptacle having a bottom wall, opposite side walls, opposite front and back walls, and a cavity, the cavity being positioned between the sidewalls and between the front and back walls, the cavity being partially bound by the bottom wall, the bottom and top walls have a plurality of apertures that extend through the bottom and top walls and that create fluid passageways into the cavity, the lid having a plurality of apertures that extend through the lid and that create additional fluid passageways into the cavity, the lid being movable between an opened position and a closed position relative to the receptacle, the lid engaging the receptacle when the lid is in the closed position and the cavity being partially bound by the lid when the lid is in the closed position and the second histological specimen cassette that has an internal chamber that creates a parallelepiped void that has a length of at least 31.75 millimeters, a width of at least 25.4 millimeters, and a height of at least 5.08 millimeters.

In another aspect of the present invention, a histological specimen cassette is disclosed. This histological specimen cassette includes a receptacle and a lid, the receptacle having a bottom wall, opposite side walls, opposite front and back walls, and a cavity, the cavity being positioned between the sidewalls and between the front and back walls, the cavity being partially bound by the bottom wall, the bottom and top walls have a plurality of apertures that extend through the bottom and top walls and that create fluid passageways into the cavity, the lid having a plurality of apertures that extend through the lid and that create additional fluid passageways into the cavity, the lid being movable between an opened position and a closed position relative to the receptacle, the lid engaging the receptacle when the lid is in the closed position and the cavity being partially bound by the lid when the lid is in the closed position, wherein the front wall slopes toward the bottom wall at an angle from about fifteen degrees to about twenty-three degrees from the bottom wall to create a writing surface to provide identification for the histological specimen cassette. This is for both the host (outer) cassette and the specimen containing inner cassette. The ability to write/label the identification on both the inner and outer cassette pair is essential to the chain of custody and positive identification (ID) for experimental and diagnostic protocol.

These are merely some of the innumerable aspects of the present invention and should not be deemed an all-inclusive listing of the innumerable aspects associated with the present invention. These and other aspects will become apparent to those skilled in the art in light of the following disclosure and accompanying drawings.

BRIEF DESCRIPTION OF DRAWINGS

For a better understanding of the present invention, reference may be made to the accompanying drawings in which:

FIG. 1 is a perspective view of the preferred embodiment of a histological examination specimen preparation cassette in accordance with the invention;

FIG. 4 is a front elevation view of the cassette shown in FIGS. 1-3;

FIG. 5 is a rear elevation view of the cassette shown in FIGS. 1-4;

FIG. 6 is a right-side elevation view of the cassette shown in FIGS. 1-5.

Figure 3:
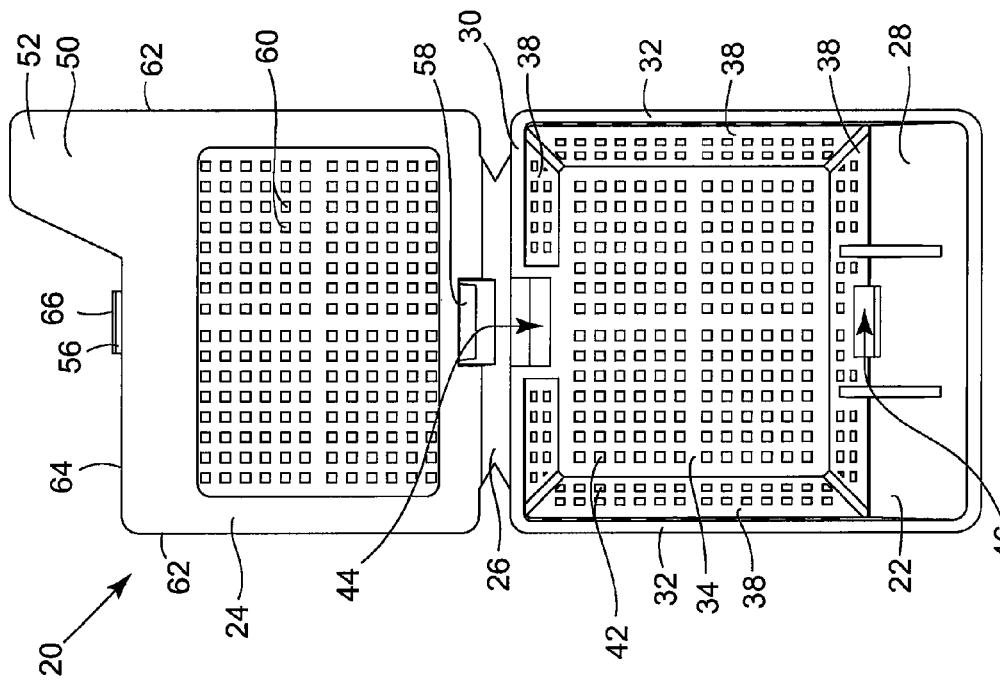
FIG. 3 is a bottom plan view of the cassette shown in FIGS. 1 and 2.
Figure 2:
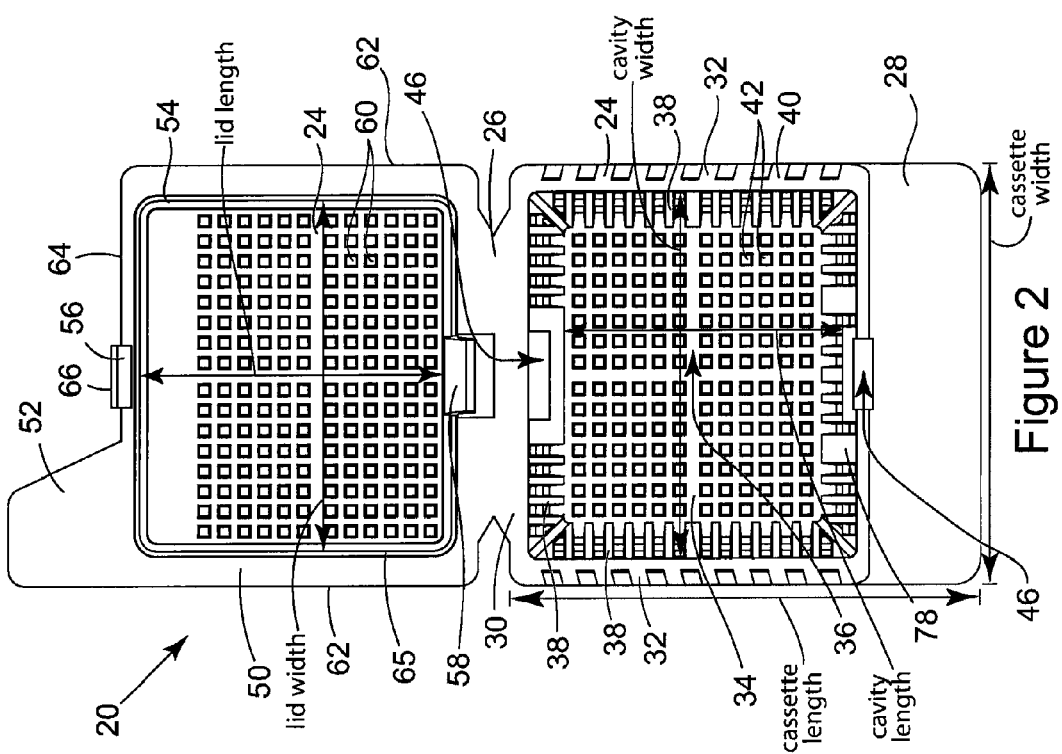
FIG. 2 is a top plan view of the cassette shown in FIG. 1.

Reference characters in the written specification indicate corresponding items shown throughout the drawing figures.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to obscure the present invention.

The preferred embodiment of a histological examination specimen preparation cassette in accordance with the invention is shown by itself in FIGS. 1-6. The cassette 20 comprises a receptacle 22 and a lid 24. The lid 24 and the receptacle 22 are preferably injection molded together out of polymeric material, which is preferably solvent resistant, as a single monolithic part in the configuration shown in FIGS. 2-6. The lid 24 is attached to the receptacle 22 via a thin bridge portion 26 that acts as a hinge and allows the lid and receptacle to pivot thereabout relative each other. However, the bridge portion 26 is configured and adapted to be frangible so that, if desired, the lid can be easily separated from the receptacle by ripping the bridge portion in half along the pivot axis.

The receptacle 22 comprises opposite front 28 and back 30 walls, opposite side walls 32, and a bottom wall 34. The receptacle 22 also comprises a cavity 36 that extends down into the receptacle and that is partially bound by the bottom wall 34 of the receptacle. The cavity 36 is further bound by four intermediate walls 38 that slope from the bottom wall 34 to the top perimeter edge 40 of the cavity. Two of the cross directed intermediate walls 38 are generally perpendicular to the back wall 30 of the receptacle 22 and diverge from each other as they extend upward. These two intermediate walls 38 eventual merge into the side walls 32 adjacent the top perimeter edge 40 of the cavity 36. The other two intermediate walls 38 are generally perpendicular to the side walls 32 of the receptacle 22 and also diverge from each other as they extend upward. One of these two intermediate walls 38 eventual merges into the back wall 30 adjacent the top perimeter edge 40 of the cavity 36, and the other of these two intermediate walls eventual merges into the front wall 28 adjacent the top perimeter edge of the cavity 36.

The outer front wall 28 slopes toward to the back wall 30 as it extends upward and is preferably oriented between fifteen and twenty-three degrees from the bottom wall 34 of the receptacle 22. More preferably, the front wall 28 is preferably oriented between sixteen and eighteen degrees from the bottom wall 34 of the receptacle 22. More preferably still, the front wall 28 is preferably oriented seventeen degrees from the bottom wall 34 of the receptacle 22. As such, the front wall 28 extends front to back more than two tenths of the front to back length of the entire receptacle 22. Each of the sidewalls 32, the bottom wall 34, and the intermediate walls 38 preferably comprises a plurality of apertures 42 to allow fluid to pass through such walls. Preferably the apertures 42 that extend through the bottom wall 34 are drafted in a manner such that the apertures increase in size as they tend from the exterior of the cassette into the cavity 36. This increases the paraffin adhesion of a tissue specimen to the exterior of the cassette 20 by creating interlocking geometry between the cassette and the solidified paraffin. The front wall 28 is preferably devoid of apertures to permit identification (ID) labeling. A first larger rectangular opening 44 preferably extends through the rear intermediate wall 38 and the lower portion of the back wall 30. A second rectangular opening 46 preferably extends down through the intersection of the front intermediate wall 38 and the front wall 30. Each of the first and second openings is centrally positioned between the side walls 32.

The lid 24 of the cassette 20 preferably comprises a main rectangular portion 50, a thumb release tab 52, a rectangular ring protrusion 54, a locking tab 56, and an arcuate guiding and locking protrusion 58. The main rectangular portion 50 of the lid 24 is preferably thin and planar and comprises a plurality of apertures 60 that extend therethrough. The thumb release tab 52 preferably extends from the front edge 64 of the main rectangular portion 50 in a coplanar manner adjacent one of the side edges 62 of the main rectangular portion. The rectangular ring protrusion 54 preferably extends downwardly (assuming the lid 24 is in its closed position as described below) from the main rectangular portion 50 in a direction generally perpendicular to the plane of the main rectangular portion. However, the rectangular ring also comprises a chamfer 65 that is angled in a manner such that the chamfer mates with the sloped intermediate walls 38 of the receptacle 22 when the lid 24 is closed. The locking tab 56 also extends downwardly from the main rectangular portion 50 adjacent the front edge 64 of the main rectangular portion and forms a locking tang 66, which can also be referred to as a finger tab, that extends forward of the front edge. The locking tab 56 is preferably centrally positioned between the side edges 62 of the main rectangular portion 50. The arcuate back guiding protrusion 58 preferably extends downward from the rectangular ring protrusion 54 and curves aft as it extends therefrom.

Figure 7:
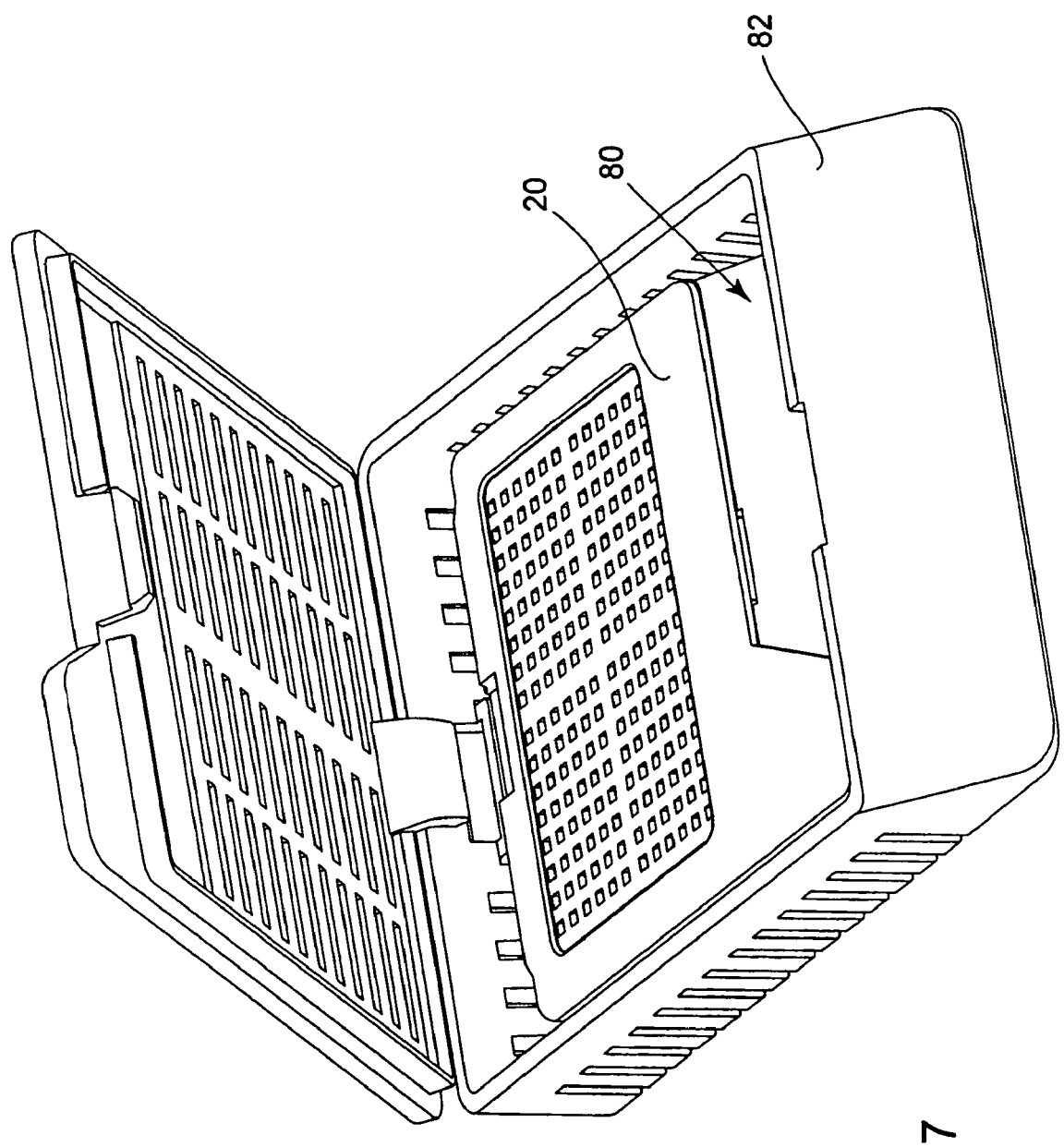
FIG. 7 is a view of an assembly comprising the cassette shown in FIGS. 1-6 positioned within the internal chamber of a prior art cassette.

As mentioned above, the lid 24 is able to pivot about the receptacle 22 by flexing the bridge portion 26. Thus, the bridge portion 26 creates a pivot axis that is parallel to and aft of the back wall the receptacle 22, and about which the lid 24 is able to pivot relative to the receptacle. When the lid 24 is in an open position relative to the receptacle 22, such as shown in FIGS. 2-6 or as shown in FIG. 1, the cavity 36 of the receptacle 22 is open from above. Alternatively, when the lid 24 is in a closed position relative to the receptacle 22, such as shown in FIG. 7, the rectangular portion 50 of the lid covers the top of the cavity 36. As the lid 24 is pivoted from an opened position to the closed position, the locking tab 56 of lid moves into the second opening 46 of the receptacle 22 where the locking tang 66 of the locking tab engages the front wall 28 of the receptacle and resiliently deflects the locking tab rearward until the locking tang reaches a position beneath the front wall. Thereafter, the locking tab 56 resiliently deflects back to its neutral position where the locking tang 66 engages against underside of the front wall 28 in a manner preventing the lid 24 from moving back to its opened position unless more than a threshold force is exerted between the lid and the receptacle 22. Alternatively, the locking tang 66 of the locking tab 56 can be configured to extend rearward from the remainder of the locking tab and to lock beneath the intermediate wall 38 adjacent the front wall 28.

Additionally, as the lid 24 is pivoted from an opened position to the closed position, the guiding protrusion 58 of the lid moves into the first opening 44 of the receptacle 22. If the bridge portion 26 is severed, the guiding protrusion 58 of the lid 24 can be inserted into the first opening 44 and used to create an alternative hinge connecting the lid to the receptacle 22. In such a case, the guiding protrusion 58 of the lid 24 interlocks with the receptacle 22 and prevents the lid from separating from the receptacle when the lid is in its closed position. When the lid 24 is in the closed position, the rectangular ring protrusion 54 of the lid extends into the cavity 36 of the receptacle 22 where it prevents tissue samples from slipping out of the cavity between the lid and receptacle. Because the chamfer 65 of the rectangular ring protrusion 54 is sloped to match the slope of the intermediate walls 38 of the receptacle 22 a face-to-face seal is created that becomes tighter in a progressive manner as the lid 24 is closed.

Moreover, when the lid 24 is in the closed position, the thumb release tab 52 extends above the front wall 28 of the receptacle 22 in a spaced apart manner. This allows a person to exert a prying force upward on the thumb release tab 52 while also pressing downward on the front wall 28 of the receptacle 22 in a manner overcoming the forward or rearward threshold force that otherwise prevents the lid 24 from moving back into an opened position.

The lid 24 and receptacle 22 are dimensioned such that the entire cassette 20, with its lid in the closed position, can be positioned within the cavity 80 of another larger cassette 82, as shown in FIG. 7. More specifically, lid 24 and receptacle 22 are dimensioned to fit within a parallelepiped void having a length of 31.75 millimeters, a width of 25.4 millimeters, and a height of 5.08 millimeters. Furthermore, the distance between the side edges 62 of the rectangular portion 50 of the lid 24 is greater than the front to back length of the rectangular portion of the lid. Additionally, the side to side width of the cavity 36 of the receptacle 22 is greater than the front to back length of the cavity. However, the overall side to side width of the cassette 20 is less than the front to back length of the entire cassette.

The above mentioned configuration the cassette 20 allows the cassette to serve the same purpose as a standard prior art cassette, without occupying as much physical space as such a prior art cassette. Additionally, the configuration the cassette 20 allows the cassette to be placed within the cavity of another prior art cassette in a manner such that the cassette can be used in tissue treatment devices that are specifically configured for prior art standard size cassettes.

Furthermore, it should be understood that when introducing elements of the present invention in the claims or in the above description of the preferred embodiment of the invention, the terms "have," "having," "includes" and "including" and similar terms as used in the foregoing specification are used in the sense of "optional" or "may include" and not as "required." Similarly, the term "portion" should be construed as meaning some or all of the item or element that it qualifies.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims that follow.

The invention claimed is:

1. An assembly comprising:
a first histological specimen cassette having a first receptacle and a first lid, the first receptacle having a bottom wall, opposite side walls, opposite front and back walls, and a cavity, the cavity being positioned between the sidewalls and between the front and back walls, the cavity being partially bound by the bottom wall, the bottom wall having a plurality of apertures that extend through the bottom wall and that create fluid passageways into the cavity, the first lid having a plurality of apertures that extend through the first lid and that create additional fluid passageways into the cavity, the first lid being movable between an opened position and a closed position relative to the first receptacle, the first lid engaging the first receptacle when the first lid is in the closed position and the cavity being partially bound by the first lid when the first lid is in the closed position; and
a second histological specimen cassette having a second receptacle and a second lid, the second receptacle having a bottom wall, opposite side walls, opposite front and back walls, and a cavity, the cavity being positioned between the sidewalls and between the front and back walls, the cavity being partially bound by the bottom wall, the bottom wall having a plurality of apertures that extend through the bottom wall and that create fluid passageways into the cavity, the second lid having a plurality of apertures that extend through the second lid and that create additional fluid passageways into the cavity, the second lid being movable between an opened position and a closed position relative to the second receptacle, the second lid engaging the second receptacle when the second lid is in the closed position and the cavity being partially bound by the second lid when the second lid is in the closed position, wherein the cavity of the second histological specimen cassette has a parallelepiped void that has a length of at least 31.75 millimeters, a width of at least 25.4 millimeters, and a height of at least 5.08 millimeters, wherein the first histological specimen cassette fits entirely within the void of the second histological specimen cassette when the second lid is in the closed position to create an assembly.

2. The assembly in accordance with claim 1, wherein the outer front wall of the first histological specimen cassette slopes toward the bottom wall at an angle from about fifteen degrees to about twenty-three degrees from the bottom wall of the first histological specimen cassette.

3. The assembly in accordance with claim 1, wherein the cavity of the first histological specimen cassette having a width measurable anywhere parallel to the pivot axis and a length measurable in any plane perpendicular to the pivot axis, the width of the cavity of the first histological specimen cassette being greater than the length of the cavity of the first histological specimen cassette.

4. An assembly comprising:
a first histological specimen cassette having a first receptacle and a first lid, the first receptacle having a bottom wall, opposite side walls, opposite front and back walls, and a cavity, the cavity being positioned between the sidewalls and between the front and back walls, the cavity being partially bound by the bottom wall, the bottom wall having a plurality of apertures that extend through the bottom wall and that create fluid passageways into the cavity, the first lid having a plurality of apertures that extend through the first lid and that create additional fluid passageways into the cavity, the first lid being movable between an opened position and a closed position relative to the first receptacle, the first lid engaging the first receptacle when the first lid is in the closed position and the cavity being partially bound by the first lid when the first lid is in the closed position, the first histological specimen cassette having a length measurable in any plane perpendicular to the pivot axis when the first lid is in the closed position, the length of the first histological specimen cassette defining a lengthwise direction, the front wall being inclined relative to the bottom wall in a manner such that the front wall extends a lengthwise distance that is at least two tenths of the length of the first histological specimen cassette; and
a second histological specimen cassette having a second receptacle and a second lid, the second receptacle having a bottom wall, opposite side walls, opposite front and back walls, and a cavity, the cavity being positioned between the sidewalls and between the front and back walls, the cavity being partially bound by the bottom wall, the bottom wall having a plurality of apertures that extend through the bottom wall and that create fluid passageways into the cavity, the second lid having a plurality of apertures that extend through the second lid and that create additional fluid passageways into the cavity, the second lid being movable between an opened position and a closed position relative to the second receptacle, the second lid engaging the second receptacle when the second lid is in the closed position and the cavity being partially bound by the second lid when the second lid is in the closed position, wherein the cavity of the second histological specimen cassette has a parallelepiped void that has a length of at least 31.75 millimeters, a width of at least 25.4 millimeters, and a height of at least 5.08 millimeters, wherein the first histological specimen cassette fits entirely within the void of the second histological specimen cassette when the first lid is in the closed position to create an assembly.

5. The assembly in accordance with claim 4, wherein the cavity of the first histological specimen cassette is partially bound by slope surfaces of the first histological specimen cassette that slope away from each other as they extend away from the bottom wall of the first histological specimen cassette, the first lid of the first histological specimen cassette comprises a sealing protrusion that extends down into the cavity of the first receptacle adjacent each of the intermediate walls when the first lid of the first histological specimen cassette is in the closed position, and the sealing protrusion comprises a chamfer that is sloped to be parallel to the sloped surfaces when the lid of the first histological specimen cassette is in the closed position.

6. An assembly comprising:

a first histological specimen cassette having a first receptacle and a first lid, the first receptacle having a bottom wall, opposite side walls, opposite front and back walls, and a cavity, the cavity being positioned between the sidewalls and between the front and back walls, the cavity being partially bound by the bottom wall, the bottom wall having a plurality of apertures that extend through the bottom wall and that create fluid passageways into the cavity, the first lid having a plurality of apertures that extend through the first lid and that create additional fluid passageways into the cavity, the first lid being movable between an opened position and a closed position relative to the first receptacle, the first lid engaging the first receptacle when the first lid is in the closed position and the cavity being partially bound by the first lid when the first lid is in the closed position, wherein the outer front wall slopes toward the bottom wall at an angle from about sixteen degrees to about eighteen degrees from the bottom wall to create a writing surface to provide identification for the first histological specimen cassette; and a second histological specimen cassette having a second receptacle and a second lid, the second receptacle having a bottom wall, opposite side walls, opposite front and back walls, and a cavity, the cavity being positioned between the sidewalls and between the front and back walls, the cavity being partially bound by the bottom wall, the bottom wall having a plurality of apertures that extend through the bottom wall and that create fluid passageways into the cavity, the second lid having a plurality of apertures that extend through the second lid and that create additional fluid passageways into the cavity, the second lid being movable between an opened position and a closed position relative to the second receptacle, the second lid engaging the second receptacle when the second lid is in the closed position and the cavity being partially bound by the second lid when the second lid is in the closed position, wherein the cavity of the second histological specimen cassette has a parallelepiped void that has a length of at least 31.75 millimeters, a width of at least 25.4 millimeters, and a height of at least 5.08 millimeters, wherein the first histological specimen cassette fits entirely within the void of the second histological specimen cassette when the first lid is in the closed position to create an assembly.

\* \* \* \* \*